United States Patent
Behrens et al.

(10) Patent No.: US 10,040,859 B2
(45) Date of Patent: Aug. 7, 2018

(54) METHODS OF TREATING HEMOPHAGOCYTIC LYMPHOHISTIOCYTOSIS WITH AN IL-33 RECEPTOR ANTIBODY

(71) Applicants: The Children's Hospital of Philadelphia, Philadelphia, PA (US); Trustees of the University of Pennsylvania, Philadelphia, PA (US)

(72) Inventors: Edward M. Behrens, West Chester, PA (US); Julia E. Rood, Philadelphia, PA (US); Taku Kambayashi, Malvern, PA (US)

(73) Assignees: The Children's Hospital of Philadelphia, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/305,272

(22) PCT Filed: Apr. 21, 2015

(86) PCT No.: PCT/US2015/026840
§ 371 (c)(1),
(2) Date: Oct. 19, 2016

(87) PCT Pub. No.: WO2015/164354
PCT Pub. Date: Oct. 29, 2015

(65) Prior Publication Data
US 2017/0037134 A1 Feb. 9, 2017

Related U.S. Application Data

(60) Provisional application No. 61/982,026, filed on Apr. 21, 2014, provisional application No. 61/993,495, filed on May 15, 2014, provisional application No. 62/146,684, filed on Apr. 13, 2015.

(51) Int. Cl.
| | | |
|---|---|---|
| A61K 39/395 | (2006.01) | |
| C07K 16/28 | (2006.01) | |
| C07K 14/54 | (2006.01) | |
| C07K 14/715 | (2006.01) | |
| A61K 38/17 | (2006.01) | |
| A61K 39/00 | (2006.01) | |

(52) U.S. Cl.
CPC ...... C07K 16/2866 (2013.01); A61K 38/1793 (2013.01); A61K 39/3955 (2013.01); C07K 14/54 (2013.01); C07K 14/7155 (2013.01); A61K 2039/505 (2013.01); C07K 2317/72 (2013.01); C07K 2317/76 (2013.01)

(58) Field of Classification Search
CPC ............ A61K 38/1793; A61K 39/3955
See application file for complete search history.

(56) References Cited

U.S. PATENT DOCUMENTS

2010/0260770 A1 10/2010 Coyle

FOREIGN PATENT DOCUMENTS

WO 2014/011984 1/2014

OTHER PUBLICATIONS

Canna, S.W., et al., "Making sense of the cytokine storm: a conceptual framework for understanding, diagnosing, and treating hemophagocytic syndromes" Pediatr. Clin. North Am. (2012) 59(2):329-44.
O'Neill, L.A.J., "The interleukin-1 receptor/Toll-like receptor superfamily: 10 years of progress" Immunol. Rev. (2008) 226:10-8.
Rood, J., et al., "Blockade of Interleukin-33 Signaling Prevents Death in a Mouse Model of Familial Hemophagocytic Lymphohistiocytosis" Arthritis and Rheumatology: Abstract Supp. 2014 ACR/ARHP Annual Meeting, Nov. 14-19, 2014, Boston, MA (2014) 66:S835-S836.
Hong, Y.S., et al. "Measurement of Interleukin-33 (IL-33) and IL-33 Receptors (sST2 and ST2L) in Patients with Rheumatoid Arthritis" J. Korean Med. Sci. (2011) 26(9):1132-1139.
Palmer, G., et al., "Inhibition of Interleukin-33 Signaling Attenuates the Severity of Experimental Arthritis" Arthritis Rheumatism (2009) 60(3):738-749.
Beherens, B.M., et al., "Interleukin 1 receptor antagonist to treat cytophagic histiocytic panniculitis with secondary hemophagocytic lymphohistiocytosis" J. Rheumatol. (2006) 33(10):2081-4.
Rood, J.E., et al., "ST2 contributes to T-cell hyperactivation and fatal hemophagocytic lymphohistiocytosis in mice" Blood (2016) 127(4):426-35.
Terrell, C.E., et al., "Perforin deficiency impairs a critical immunoregulatory loop involving murine CD8+ T cells and dendritic cells" Blood (2013) 121(26):5184-91.
Krebs, P., et al., "Disruption of MyD88 signaling suppresses hemophagocytic lymphohistiocytosis in mice" Blood (2011) 117(24):6582-8.
Bonilla, W.V., et al., "The Alarmin Interleukin-33 Drives Protective Antiviral CD8+ T Cell Responses" Science (2012) 335(6071):984-9.
Bourgeois, E., et al., "The pro-Th2 cytokine IL-33 directly interacts with invariant NKT and NK cells to induce IFN-gamma production" Eur. J. Immunol. (2009) 39(4):1046-55.
Yang, Q., et al. "IL-33 synergizes with TCR and IL-12 signaling to promote the effector function of CD8+ T cells" Eur. J. Immunol. (2011) 41(11):3351-60.
Lykens, J.E., et al., "Perforin is a critical physiologic regulator of T-cell activation" Blood (2011) 118(3):618-26.
Jordan, M.B., et al., "An animal model of hemophagocytic lymphohistiocytosis (HLH): CD8+ T cells and interferon gamma are essential for the disorder" Blood (2004) 104(3):735-43.
Tesi, B., et al., "Hemophagocytic lymphohistiocytosis in 2 patients with underlying IFN-gamma receptor deficiency" J. Allergy Clin. Immunol. (2015) 135(6):1638-41.

(Continued)

*Primary Examiner* — Prema Mertz
(74) *Attorney, Agent, or Firm* — Robert C. Netter, Jr.; Dann, Dorfman, Herrell & Skillman

(57) ABSTRACT

Compositions and methods for treating a cytokine release syndrome such as chimeric antigen receptor T-cell cytokine release syndrome or hemophagocytic lymphohistiocytosis are provided.

9 Claims, 13 Drawing Sheets

(56) References Cited

OTHER PUBLICATIONS

Figure 1:
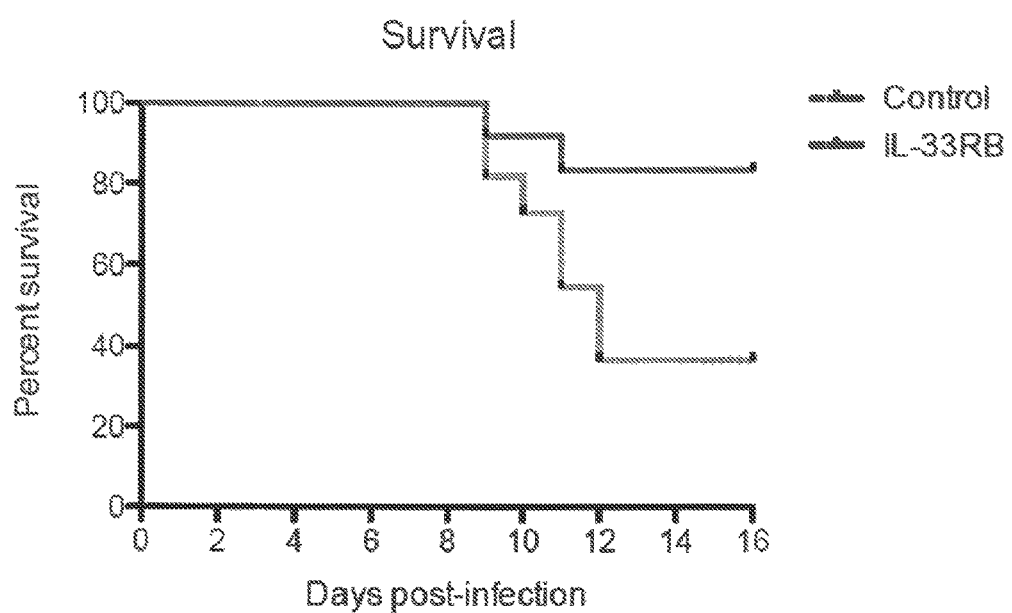

Oboki, K., et al., "IL-33 is a crucial amplifier of innate rather than acquired immunity" Proc. Natl. Acad. Sci., (2010) 107(43):18581-6.

Zhang, Y., et al., "IL-33/ST2 Correlates with Severity of Haemorrhagic Fever with Renal Syndrome and Regulates the Inflammatory Response in Hantaan Virus-Infected Endothelial Cells" PLoS Negl. Trop. Dis. (2015) 9(2):e0003514.

METHODS OF TREATING HEMOPHAGOCYTIC LYMPHOHISTIOCYTOSIS WITH AN IL-33 RECEPTOR ANTIBODY

This application is a § 371 application of PCT/US2015/026840, filed Apr. 21, 2015, which claims priority under 35 U.S.C. § 119(e) to U.S. Provisional Patent Application No. 61/982,026, filed Apr. 21, 2014; U.S. Provisional Patent Application No. 61/993,495, filed May 15, 2014; and U.S. Provisional Patent Application No. 62/146,684, filed Apr. 13, 2015. The foregoing applications are incorporated by reference herein.

This invention was made with government support under Grant No. HL112836-01A1 awarded by the National Heart, Lung, and Blood Institute. The Government has certain rights in this invention.

FIELD OF THE INVENTION

The present invention relates to the field of cytokine-related diseases or disorders. Specifically, compositions and methods for inhibiting, treating, and/or preventing cytokine-related diseases or disorders, e.g., hemophagocytic lymphohistiocytosis or chimeric antigen receptor T-cell cytokine release syndrome, are disclosed.

BACKGROUND OF THE INVENTION

Several publications and patent documents are cited throughout the specification in order to describe the state of the art to which this invention pertains. Each of these citations is incorporated herein by reference as though set forth in full.

Familial hemophagocytic lymphohistiocytosis (FHL) is a life-threatening disorder caused by genetic defects in perforin (FHL type 2, or FHL2) or other proteins in the granule exocytosis pathway (Stepp et al. (1999) Science 286(5446): 1957-1959; Brisse et al. (2014) Cytokine Growth Factor Rev., S1359-6101(14)00129-4). Due to the absence of immune-mediated cytotoxicity in these patients, viral infections and other inflammatory stimuli trigger an ineffective but hyperactive immune response that rapidly leads to fatal immunopathology, described clinically as hemophagocytic syndrome (Janka et al. (2014) Blood Rev., 28(4):135-142). Hemophagocytic lymphohistiocytosis (HLH) manifests as a "cytokine storm" with elevated inflammatory cytokines, particularly IFNγ, followed by multi-organ failure, pancytopenia, and ultimately death. The difficulty in treating FHL and related hemophagocytic syndromes stems from both the lack of effective therapies and incomplete understanding of the underlying pathophysiology.

Studies of the FHL2 murine model, in which lymphocytic choriomeningitis virus (LCMV) infection of perforin-deficient ($Prf1^{-/-}$) mice induces disease, demonstrate that pathologic inflammation is driven by an excess of IFNγ-producing LCMV-specific CD8$^+$ T cells (Jordan et al. (2004) Blood 104(3):735-743; Lykens et al. (2011) Blood 118(3):618-626; Matloubian et al. (1999) J. Virol., 73(3):2527-2536). It is thought that the inability of these CD8$^+$ T-cells to kill their targets leads to an over stimulation of these cells by antigen-presenting cells (APCs), and the resultant elevated IFNγ and clinical syndrome. While this overactive T cell response is attributed to excess antigen stimulation through the T cell receptor (TCR) (Terrell et al. (2013) Blood 121(26):5184-5191), data has also shown that non-TCR, MyD88-dependent signaling pathways may be equally important (Krebs et al. (2011) Blood 117(24):6582-6588). Furthermore, the majority of FHL patients do not develop hemophagocytic syndrome until after several months of age (Jessen et al. (2013) Front. Immunol., 4:448), long after they have encountered antigenic pathogens in the environment, consistent with a requirement for additional signals beyond antigen to induce the hyperinflammatory immune response. Improved methods of treating and/or preventing HLH are needed.

SUMMARY OF THE INVENTION

In accordance with the present invention, compositions and methods for inhibiting, treating, and/or preventing a cytokine-related disease or disorder, particularly a cytokine release syndrome (e.g., one characterized by increased IFNγ) such as hemophagocytic lymphohistiocytosis or cytokine release syndrome (e.g., chimeric antigen receptor T-cell cytokine release syndrome), are provided. In a particular embodiment, the method comprises administering an inhibitor of IL-33 signaling to the subject. In a particular embodiment, the method comprises administering to a subject an antibody or fragment thereof immunologically specific for the IL-33 receptor (IL-33R) or IL-33.

BRIEF DESCRIPTIONS OF THE DRAWING

FIG. 1 provides a graph of the survival of perforin knockout (perforin$^{-/-}$) mice after intraperitoneal (i.p.) infection with 2×10$^5$ plaque-forming units (PFU) LCMV-Armstrong. Mice received 150 µg i.p. of either IL-33RB (n=12) or isotype control antibody (n=11) every other day, beginning on day 3 post-infection. Some mice were sacrificed on day 11 for further analysis and were censored from the survival analysis on that day. Survival was compared using the log rank test.

Figure 2:
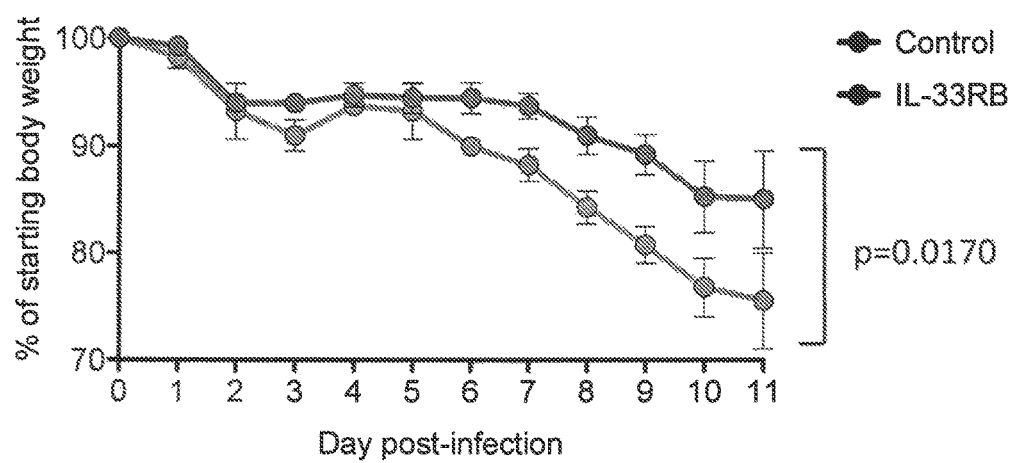

FIG. 2 provides a graph of the weight loss of perforin knockout mice after i.p. infection with 2×10$^5$ PFU LCMV-Armstrong. Mice received 150 µg i.p. of either IL-33RB (n=4) or isotype control antibody (n=4) on days 3, 5, and 8. Surviving mice were euthanized on day 11 for further analysis when one mouse in the Control group died. Curves were analyzed for significant interaction by 2-way ANOVA.

Figure 3A:
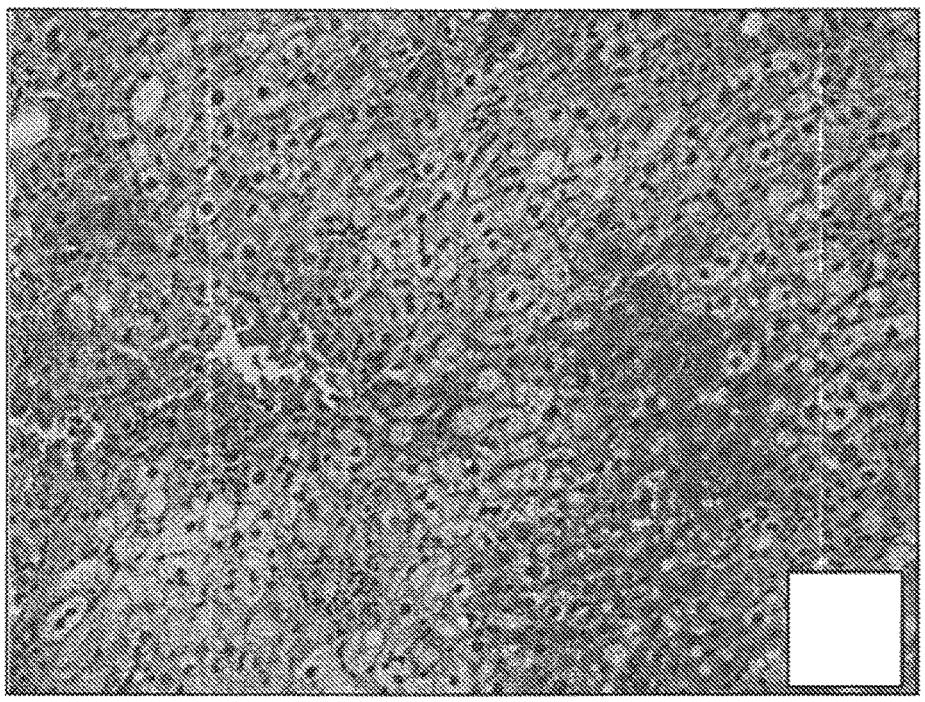
Figure 3B:
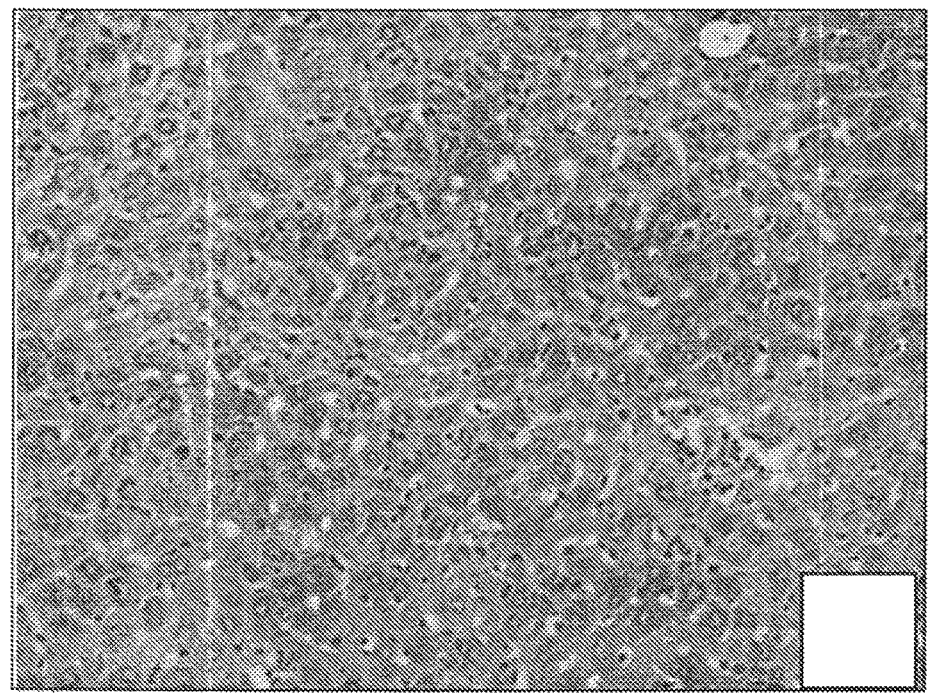

FIGS. 3A and 3B provide images of liver parenchymal damage of perforin knockout mice after i.p. infection with 2×10$^5$ PFU LCMV-Armstrong and treatment with either isotype control antibody or IL-33RB treated mice. Mice received 150 µg i.p. of either IL-33RB (FIG. 3B) or isotype control antibody (FIG. 3A) on days 3, 5, and 8. Mice were euthanized on day 11 and livers examined by H&E stain. Representative pictures are shown. Magnification 200×.

Figure 4:
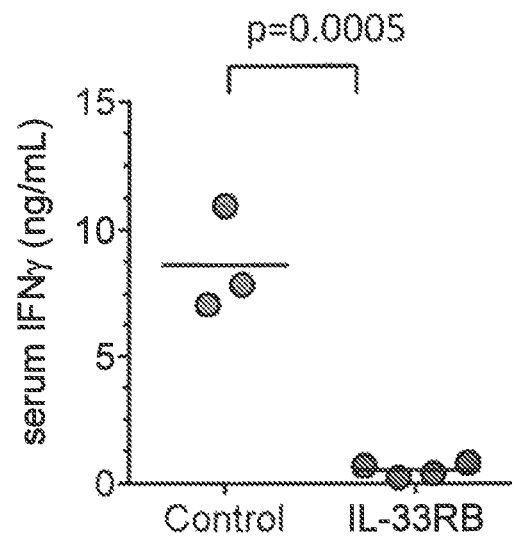

FIG. 4 provides a graph of serum IFNγ levels in LCMV-infected perforin knockout mice treated with either IL-33RB (n=4) or isotype control (n=4). Serum IFNγ levels were determined by ELISA on day 11 post-infection.

Figure 5A:
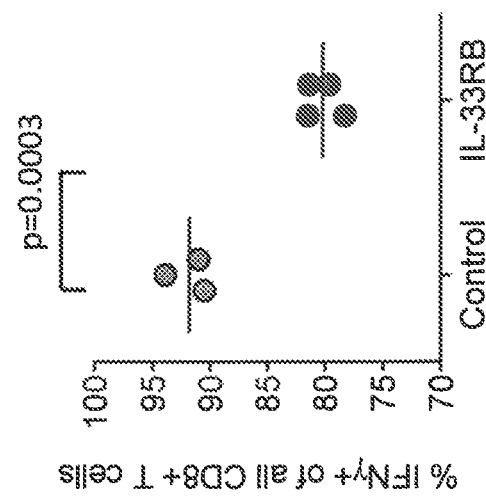
Figure 5B:
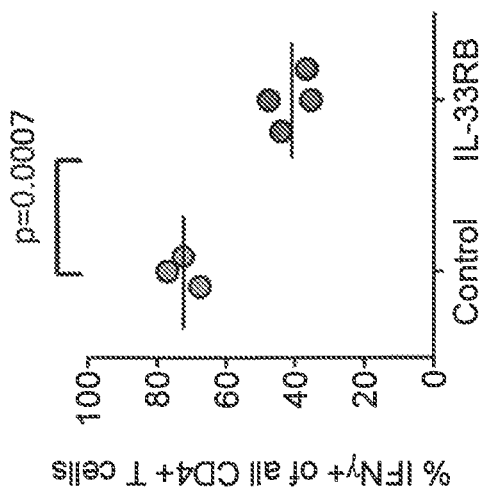
Figure 5C:
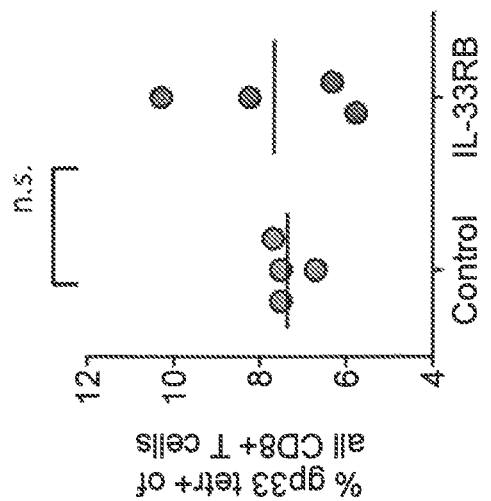

FIGS. 5A-5C demonstrate that IL-33R blockade reduces the frequency of T cells capable of producing IFNγ. LCMV-infected perforin knockout mice were treated with either IL-33R blocking antibody (n=3) or isotype control (n=4). On day 11, splenocytes were harvested. An aliquot was stained for T-cell markers and gp33 tetramer to look for LCMV reactive CD8+ T-cells (FIG. 5A). The rest of the cells were stimulated with PMA and ionomycin in vitro for 5 hours in the presence of brefeldin A. Cells were then fixed and stained for intracellular IFNγ. The frequency of CD4+

T cells (FIG. 5B) and CD8+ T cells (FIG. 5C) expressing IFNγ were determined. Results of unpaired student's t test are indicated.

Figure 6:
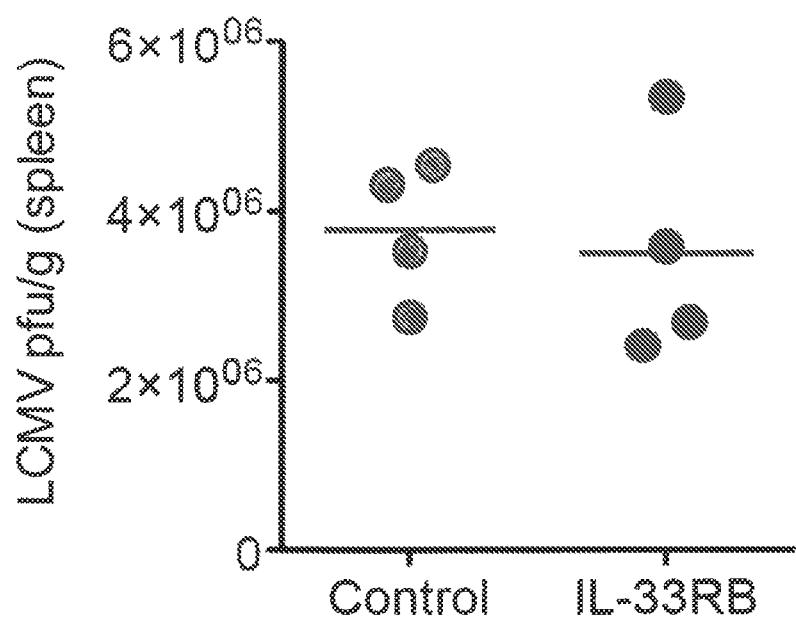

FIG. 6 provides a graph of splenic LCMV titers, 11 days post-infection, in perforin knockout mice treated with IL-33R blocking antibody or isotype control.

Figure 7A:
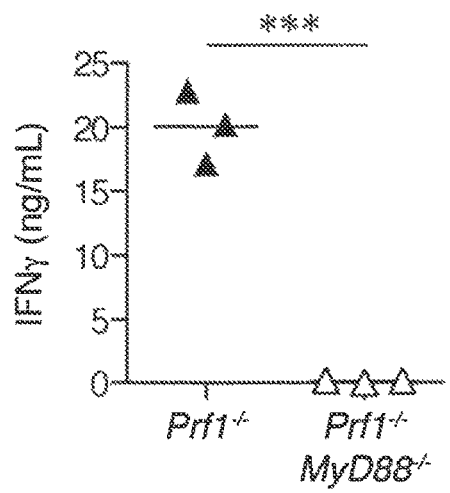
Figure 7B:
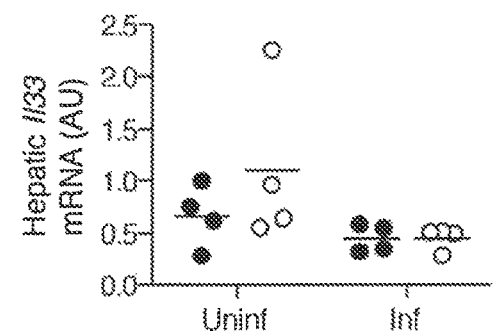
Figure 7B:
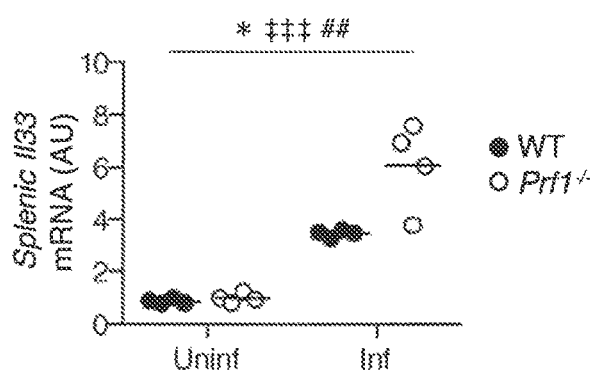
Figure 7C:
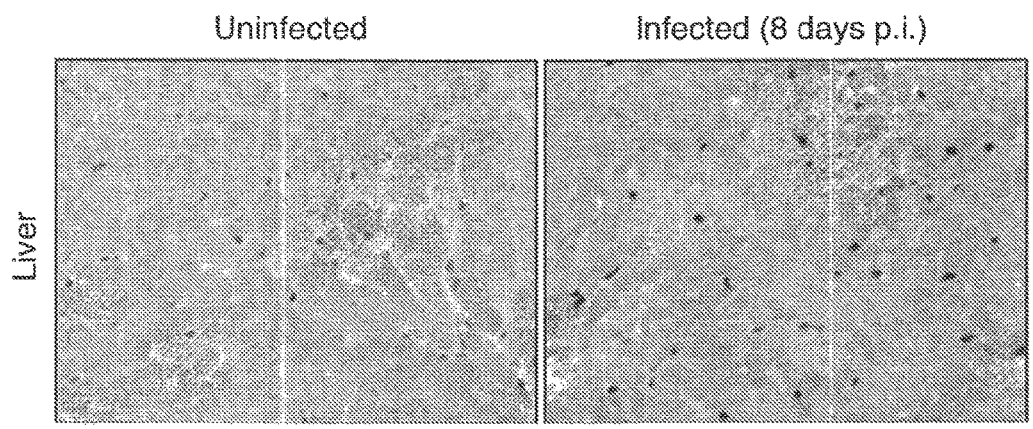
Figure 7D:
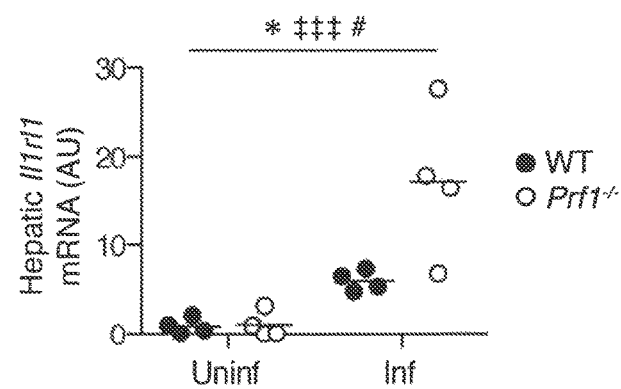
Figure 7D:
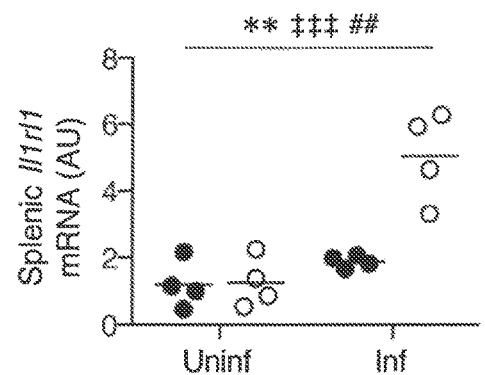

FIGS. 7A-7D show that MyD88-dependent signals, including IL-33, are important in the murine model of FHL2. $Prf1^{-/-}$, $Prf1^{-/-}MyD88^{-/-}$, or WT mice were infected with $2\times10^5$ PFU LCMV-Armstrong i.p. on day 0. Symbols represent individual mice. FIG. 7A: Serum IFNγ levels in $Prf1^{-/-}$ and $Prf1^{-/-}MyD88^{-/-}$ mice 8 days p.i. N=3. Analyzed by 2-tailed t-test. FIG. 7B: Expression of Il33 at days 0 (Uninf) and 7 p.i. (Inf). AU, arbitrary units. Analyzed by 2-way ANOVA. Significance of terms is denoted as follows: #, Genotype (WT vs. $Prf1^{-/-}$); ‡LCMV (Uninf vs. Inf); *, Interaction between Genotype and LCMV. N=1. FIG. 7C: Immunohistochemical staining of IL-33 in $Prf1^{-/-}$ mice, shown at 200× magnification. Representative of 4 mice/group. FIG. 7D: Expression of Il1rl1 (ST2 gene), analyzed as in FIG. 7B. N=1.

Figure 8A:
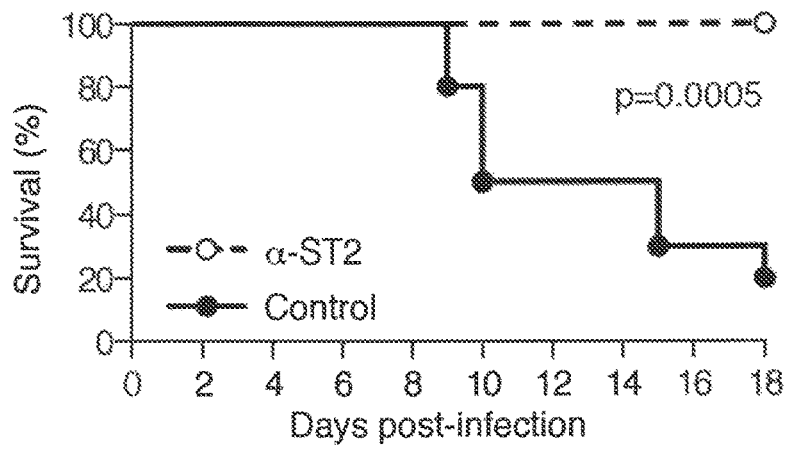
Figure 8B:
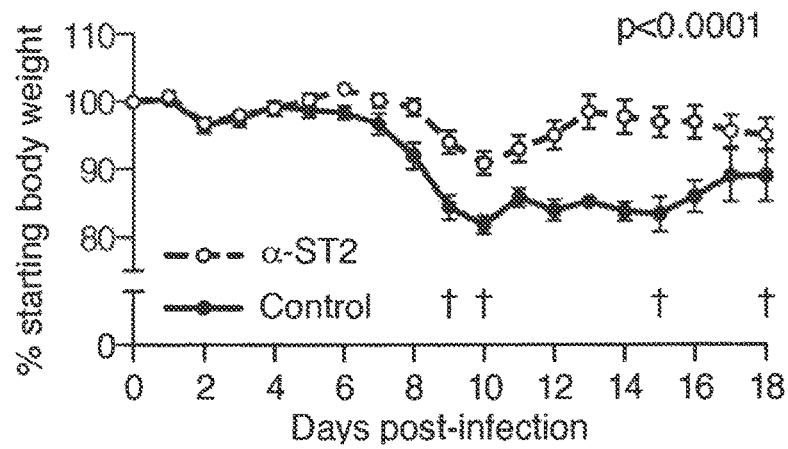
Figure 8C:
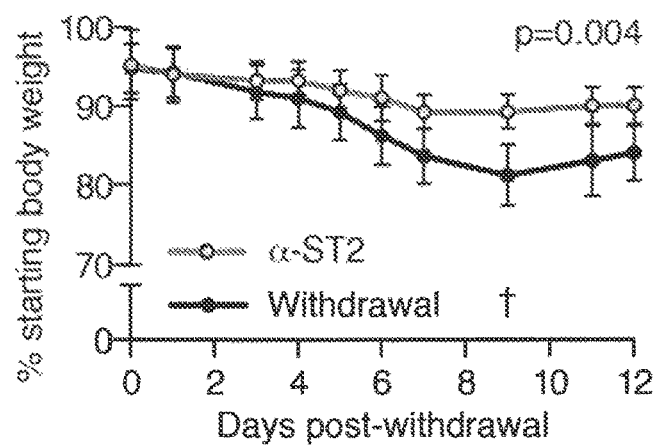
Figure 8D:
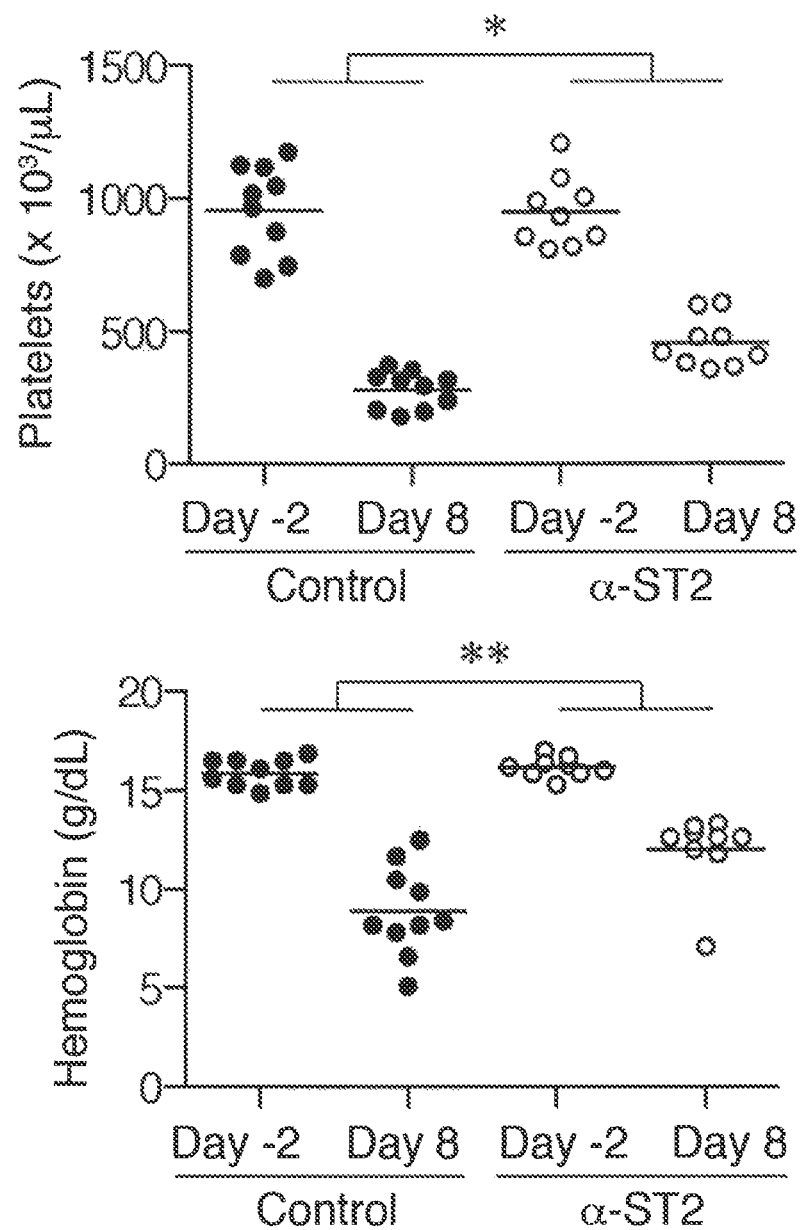
Figure 8E:
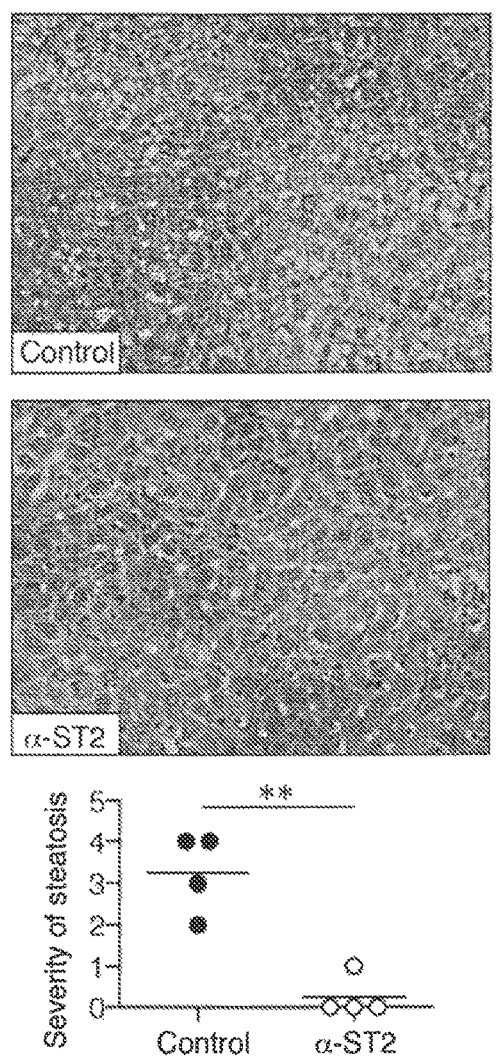
Figure 8F:
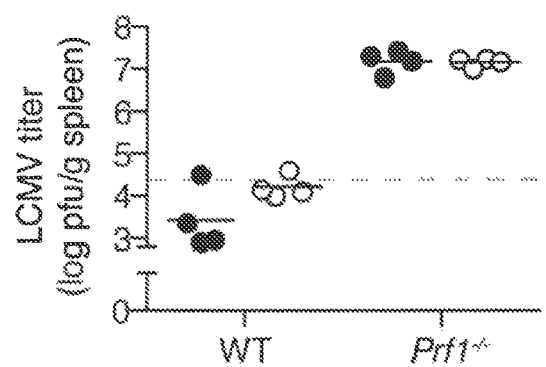

FIGS. 8A-8F show that ST2 blockade reduces morbidity and mortality in FHL2 mice despite the persistence of LCMV. $Prfr1^{-/-}$ mice were infected with $2\times10^5$ PFU LCMV-Armstrong i.p. on day 0 to induce FHL. On day 3 p.i. and every other day thereafter, mice were injected with 150 μg i.p. of either α-ST2 or Control antibody. FIG. 8A: Survival of α-ST2-treated (n=9) and Control (n=10) mice. Moribund mice were euthanized according to IACUC protocol. Analyzed by log-rank test. FIG. 8B: Body weight of α-ST2-treated and Control mice. Symbols represent mean±SEM of 9-10 mice. † indicates timepoints at which Control mice died and were excluded from subsequent weight analysis. N=2. Analyzed by mixed linear effects model; significance of Interaction term (α-ST2 vs. Control over time) is indicated. FIG. 8C: Body weight of mice withdrawn from α-ST2 treatment at day 18 p.i. (Withdrawal) or receiving continued α-ST2 treatment. Symbols represent mean±SEM of 4-5 mice. † indicates timepoints at which Withdrawal mice died and were excluded from subsequent weight analysis. N=1. Analyzed by mixed linear effects model; significance of Interaction term (α-ST2 vs. Withdrawal over time) is indicated. FIG. 8D: Platelet and hemoglobin levels from peripheral blood of α-ST2-treated and Control mice 2 days prior to infection and 8 days p.i. N=2. Analyzed by repeated measures 2-way ANOVA; significance of Interaction term (α-ST2 vs. Control over time) is indicated. FIG. 8E: Representative H&E-stained liver sections from Control and α-ST2-treated mice, 200× magnification. Severity of microvesicular steatosis was scored on day 8 p.i. and analyzed by student's 2-tailed t-test. N=2. FIG. 8F: Splenic LCMV titer 8 days p.i. in Control and α-ST2-treated mice. LCMV-infected WT mice were included for comparison. Dotted line indicates limit of detection of plaque assay. N=2. No significant differences between Control and α-ST2-treated mice for either genotype by unpaired t-test.

Figure 9A:
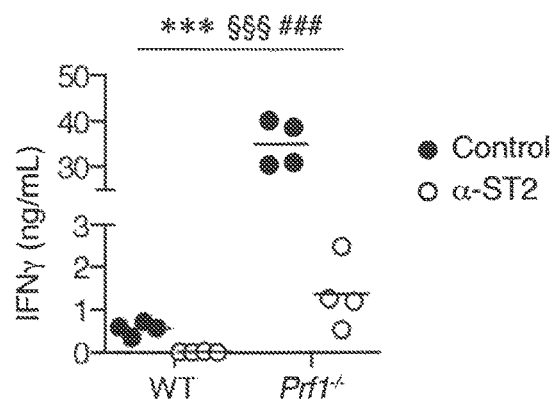
Figure 9B:
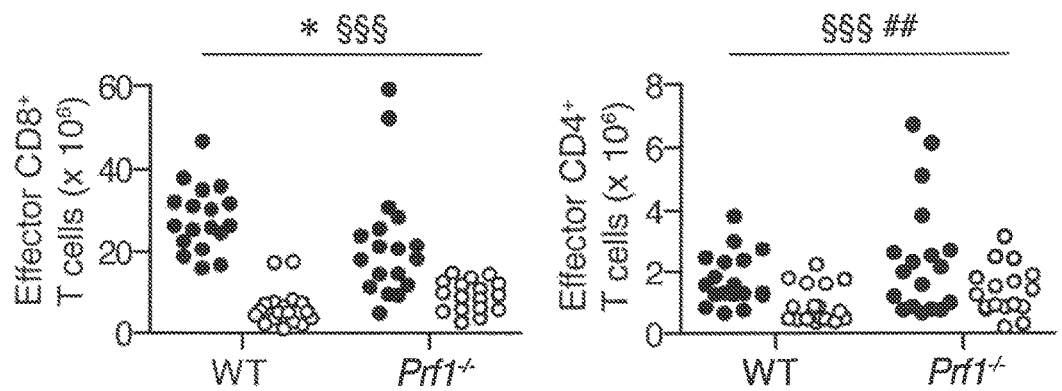
Figure 9C:
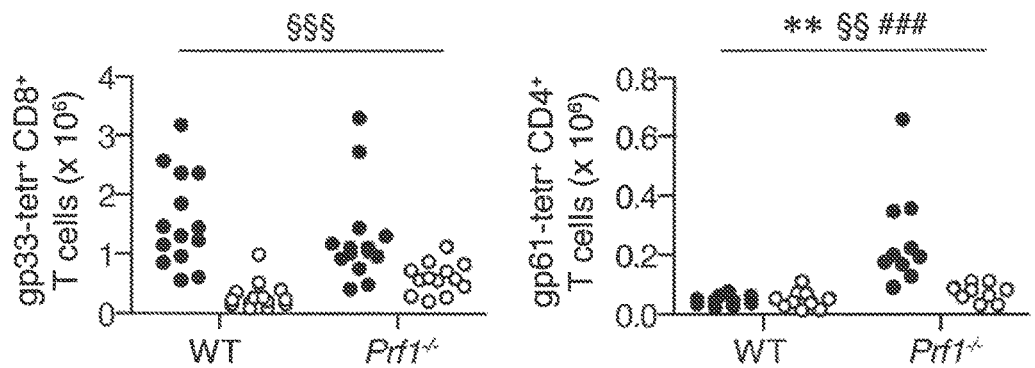
Figure 9D:
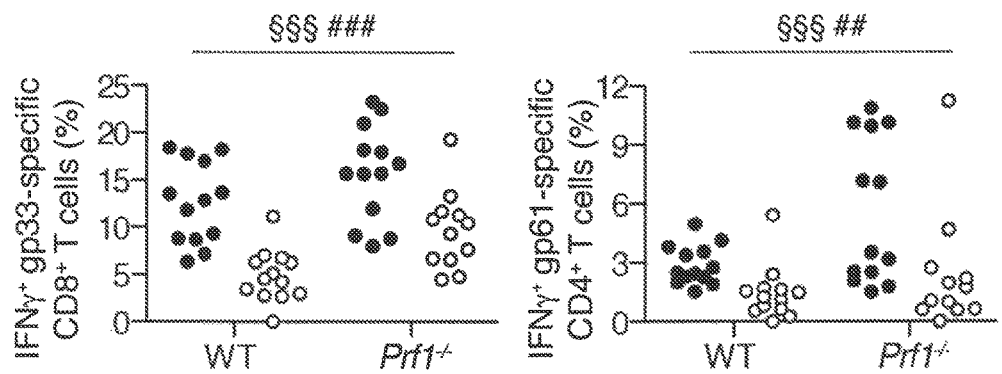

FIGS. 9A-9E show that ST2 blockade reduces IFNγ production by T cells. WT and $Prf1^{-/-}$ mice were infected with $2\times10^5$ PFU LCMV-Armstrong i.p. on day 0, injected with 150 μg i.p. of either α-ST2 or Control antibody on days 3, 5, and 7, and analyzed on day 8. FIG. 9A: Serum IFNγ level. N=3. FIG. 9B: Numbers of splenic $CD44^{hi}CD62L^{lo}CD127^{lo}$ effector T cells. FIG. 9C: Numbers of splenic LCMV-specific T cells staining with gp33 MHC Class I tetramer or gp66 MHC Class II tetramer. FIG. 9D: Frequency of T cells producing IFNγ in response to in vitro restimulation with LCMV peptides (above background).

Figure 9E:
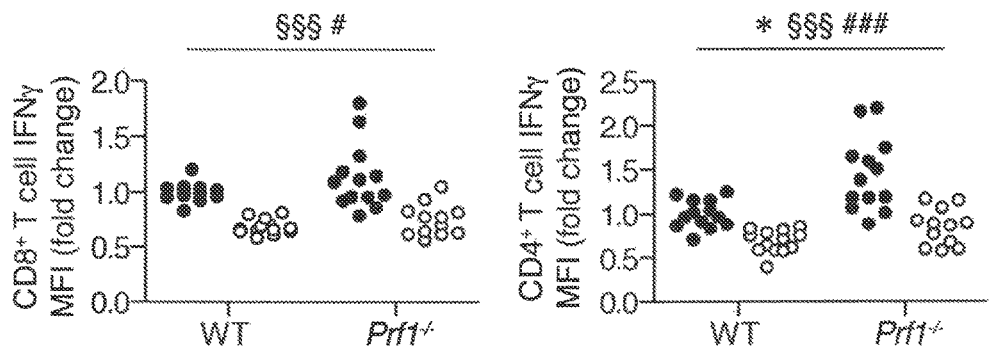

FIG. 9E: Median IFNγ fluorescence intensity of IFNγ+ T cells after in vitro peptide restimulation, normalized to WT Control mean for each experiment. Analyzed by 2-way ANOVA (FIG. 9A) or by mixed linear effects modeling of data pooled from 2-4 experiments (FIGS. 9B-9E). Significance of terms is denoted as follows: #, Genotype (WT vs. Prf1–/–); §, Treatment (Control vs. α-ST2); *, Interaction between Genotype and Treatment.

DETAILED DESCRIPTION OF THE INVENTION

IL33 is an inflammatory cytokine that is released by normal tissues upon damage. IL33 receptors are classically thought to be on CD4+ T-cells. IL-33 has also been identified as a critical cytokine for the promotion of anti-viral CD8+ T-cell responses, acting as an "alarmin" to communicate tissue damage to the immune system and, thus, the need for a response (Bonilla et al. (2012) Science 335:984-9).

Herein, it is shown that blocking IL33 signaling, particularly the IL33 receptor, in a murine model of HLH (perforin deficient ($pfn^{-/-}$) mice infected with LCMV) results in improvement in weight loss, survival, and a dramatic decrease in the production of the pathogenic IFNγ to almost normal levels. This is accompanied by a reduction in the numbers of IFNγ producing CD4+ and CD8+ T-cells. These results indicate that inhibiting or blocking the IL33 receptor and/or IL33 results in the reduction and/or prevention of morbidity and mortality in subjects with a cytokine-related disease or disorder. Blocking IL33 signaling is a novel therapeutic target in cytokine-related diseases or disorders, providing a completely different means of treatment than any therapeutic currently available or in development for the disease. Further, the targeting of IL33 will not have the side effect profile observed with current therapies such as glucocorticoids, cyclosporine A, and etoposide because it is more specific and will not inhibit the entire immune system, thereby reducing the potential for infectious side effects.

The instant invention encompasses methods of inhibiting, treating, and/or preventing a cytokine-related disease or disorder, particularly hemophagocytic lymphohistiocytosis or chimeric antigen receptor T-cell cytokine release syndrome, in a subject in need thereof. In a particular embodiment, the subject is undergoing an active flare (e.g., cytokine storm) of the cytokine-related disease or disorder (e.g., hemophagocytic lymphohistiocytosis or chimeric antigen receptor T-cell cytokine release syndrome). The methods of the instant invention can be co-administered (sequentially and/or simultaneously) with at least one other therapeutic for the treatment of the cytokine-related disease or disorder (e.g., hemophagocytic lymphohistiocytosis or chimeric antigen receptor T-cell cytokine release syndrome). For example, current therapeutic modalities for hemophagocytic lymphohistiocytosis include, without limitation, immunosuppressants, glucocorticoids, cyclosporine A, etoposide, methotrexate, IL-1 (e.g., IL-1 beta) blocking agent or blockade (e.g., anakinra (Kineret®), rilonacept, canakinumab, and gevokizumab), and bone marrow transplant. In a particular embodiment, the subject to be treated has received (or is undergoing or will soon undergo) chimeric antigen receptor T-cell therapy (e.g., for the treatment of a B cell malignancy).

While the instant invention exemplifies methods of treating, inhibiting, and/or preventing hemophagocytic lymphohistiocytosis, the compositions and methods may be used to treat or inhibit other cytokine-related diseases or disorders, particularly those characterized by a "cytokine storm" or elevated levels of cytokines (e.g., compared to a normal or healthy subject without the cytokine-related disease or disorder or compared to the subject prior to having the cytokine-related disease or disorder). In a particular embodiment, the cytokine-related disease or disorder is characterized by elevated IFNγ levels. Examples of other cytokine-related diseases or disorders include, without limitation, macrophage activation syndrome, systemic inflammatory response syndrome (SIRS), sepsis, chimeric antigen receptor T-cell cytokine release syndrome, and malignancy associated hemophagocytic lymphohistiocytosis. In a particular embodiment of the instant invention, the methods further comprise monitoring the cytokine-related disease or disorder of the subject (e.g., before, during, and/or after therapy by the methods of the instant invention).

Hemophagocytic lymphohistiocytosis (also known as hemophagocytic syndrome) comprises familial (primary) hemophagocytic lymphohistiocytosis (FHL) and secondary HLH (SHLH). HLH is a hematologic disorder that is typically characterized with fever, splenomegaly, cytopenia, elevated ferritin, elevated triglycerides or decreased fibrinogen, hemophagocytosis, low NK cell activity, and/or elevated soluble IL-2 receptor. The presence of at least about five of these symptoms is typically required for diagnosis. HLH may also be characterized by other symptoms such as liver function test abnormalities, jaundice, rash, coagulopathy, lymphocytosis, and/or histiocytosis. HLH may also be screened for through detection of at least one biomarker such as, without limitation: ferritin, soluble IL-2 receptor, IFNγ, complete blood count, fibrinogen, erythrocyte sedimentation rate (ESR), and/or C-reactive protein (CRP). HLH may be monitored (e.g., before, during and/or after therapy with an IL-33 pathway inhibitor) by measuring at least one of the above biomarkers or symptoms and/or monitoring at least one of blood pressure, liver function, renal function, fever, rash, and splenomegaly.

Chimeric antigen receptors are fusion proteins comprising antigen recognition moieties and T cell-activation domains. CD19 CARs consisting of a CD19-specific binding domain have been shown to be effective against B-cell malignancies such as chronic lymphocytic leukemia and acute lymphocytic leukemia (Porter et al. (2011) N. Engl. J. Med., 365:725-33; Grupp et al. (2013) N. Engl. J. Med., 368:1509-18). However, cytokine release syndrome (CRS) is a common—and potentially lethal—complication of CAR T-cell therapy. Generally, CRS is an array of inflammatory symptoms associated with elevated cytokine levels (e.g., IL-2R, MCP-1, MIP1B, IL-10, IL-6, and/or IFN-γ; particularly IL-10, IL-6, and/or IFN-γ)—although the severity of CRS does not necessarily correlate with the degree of elevation of each cytokine. CRS symptoms range from mild symptoms such as fever, myalgia, and flu-like symptoms to severe symptoms such as high fevers, hepatosplenomegaly, liver dysfunction, hypofibrinogenemia, hyperferritinemia, vascular leakage, hypotension, pulmonary edema, coagulopathy, and organ or multi-organ failure. These symptoms may be monitored before, during and/or after therapy with an IL-33 pathway inhibitor.

In a particular embodiment, the methods of the instant invention comprise administering an IL-33 pathway inhibitor to a subject. In a particular embodiment, the inhibitor is an antibody or fragment thereof immunologically specific for IL-33R (also known as Interleukin 1 receptor-like 1 (IL1RL1) or ST2; PubMed Gene ID: 9173 provides examples of nucleic acid and amino acid sequences of IL-33R, including isoforms and variants) or IL-33 (PubMed Gene ID: 90865 provides examples of nucleic acid and amino acid sequences of IL-33, including isoforms and variants). In a particular embodiment, the inhibitor is a polypeptide or peptide which specifically binds IL-33R or IL-33. In a particular embodiment, the inhibitor is a small molecule inhibitor. In a particular embodiment, the inhibitor is a soluble form of IL-33R (e.g., the extracellular domain; see, e.g., Iwahana et al. (1999) Eur. J. Biochem., 264:397-406; Palmer et al. (2009) Arthritis Rheumat., 60:738-749; Hayakawa et al. (2007) J. Biol. Chem., 282:26369-26380). In a particular embodiment, the inhibitor is an antisense or an interfering nucleic acid molecule (e.g., siRNA or shRNA) directed specifically against IL-33R or IL-33.

In certain embodiments, the IL-33 pathway inhibitor is an antigen binding protein, e.g., an antibody or fragment thereof, immunologically specific for IL-33R. It is contemplated that such antibodies or fragments thereof may bind IL-33R and block binding of the receptor to IL-33 or such antibodies or fragments thereof may bind the IL-33R-IL-33 complex and block the recruitment of the signaling co-receptor AcP. Examples of IL-33R binding proteins (e.g., antibodies) include but are not limited to those described in U.S. Pat. Nos. 7,087,396, 7,452,980, and 8,444,987; WO 2013/165894; WO 99/34217; WO 2013/173761; and U.S. Patent Application Publication Nos. 20130287777, 20130336980, and 20140004107 (all incorporated herein by reference in their entirety, particularly for the IL-33R binding proteins/antibodies described therein). In a particular embodiment, the IL-33R binding protein is an antibody described in U.S. Patent Application Publication No. 20130287777 (e.g., an antibody or fragment thereof that comprises the HCDR1, the HCDR2, the HCDR3, the LCDR1, the LCDR2, and the LCDR3 of what is set forth therein as SEQ ID NOs: 97, 114, 84, 130, 90, and 134, respectively). In a particular embodiment, the IL-33R binding protein is an antibody described in U.S. Patent Application Publication No. 20140004107 (e.g., Ab1, Ab2, Ab3, Ab4, Ab5, Ab6, Ab7, Ab8, Ab9, Ab10, Ab11, Ab30, Ab32, or Ab33 or a functional fragment or derivative thereof).

In a particular embodiment, the IL-33 pathway inhibitor is an antigen binding protein, e.g., an antibody or fragment thereof, immunologically specific for IL-33. It is contemplated that such antibodies or fragments thereof may bind IL-33 and block binding of the cytokine to IL-33R or such antibodies or fragments thereof may bind the IL-33r-IL-33 complex and block recruitment of the signaling co-receptor AcP. Examples of IL-33 binding proteins include but are not limited to those described in U.S Patent Application Publication No. 20140271658, WO 2014/152195, and WO 2014/164959 (all incorporated herein by reference in their entirety, particularly for the IL-33 binding proteins/antibodies described therein).

The antibody may be a naturally occurring antibody or may be a synthetic or modified antibody (e.g., a recombinantly generated antibody; a chimeric antibody; a bispecific antibody; a humanized antibody; a camelid antibody; and the like). The antibody may comprise at least one purification tag. In a particular embodiment, the framework antibody is an antibody fragment. Antibody fragments include, without limitation, immunoglobulin fragments including, without limitation: single domain (Dab; e.g., single variable light or heavy chain domain), Fab, Fab', F(ab')$_2$, and F(v); and fusions (e.g., via a linker) of these immunoglobulin fragments including, without limitation: scFv, scFv$_2$, scFv-Fc, minibody, diabody, triabody, and tetrabody. The antibody may also be a protein (e.g., a fusion protein) comprising at least one antibody or antibody fragment. In a particular embodiment of the instant invention, the antibody is a monoclonal antibody or fragment thereof. The antibody may also be a synthetic protein which mimics an immunoglobulin. Examples include, without limitation, Affibody® molecules (Affibody, Bromma, Sweden), darpins (designed ankyrin repeat proteins; Kawe et al. (2006) J. Biol. Chem., 281:40252-40263), and peptabodies (Terskikh et al. (1997) PNAS 94:1663-1668).

The antibodies of the instant invention may be further modified. For example, the antibodies may be humanized. In a particular embodiment, the hybrid antibodies (or a portion thereof) are inserted into the backbone of an antibody or antibody fragment construct. For example, the variable light domain and/or variable heavy domain of the antibodies of the instant invention may be inserted into another antibody construct. Methods for recombinantly producing antibodies are well-known in the art. Indeed, commercial vectors for certain antibody and antibody fragment constructs are available.

The antibody molecules of the invention may be prepared using a variety of methods known in the art. Polyclonal and monoclonal antibodies may be prepared as described in Current Protocols in Molecular Biology, Ausubel et al. eds. Antibodies may be prepared by chemical cross-linking, hybrid hybridoma techniques and by expression of recombinant antibody fragments expressed in host cells, such as bacteria or yeast cells. In one embodiment of the invention, the antibody molecules are produced by expression of recombinant antibody or antibody fragments in host cells. The nucleic acid molecules encoding the antibody may be inserted into expression vectors and introduced into host cells. The resulting antibody molecules are then isolated and purified from the expression system. The antibodies optionally comprise a purification tag by which the antibody can be purified. The purity of the antibody molecules of the invention may be assessed using standard methods known to those of skill in the art, including, but not limited to, ELISA, immunohistochemistry, ion-exchange chromatography, affinity chromatography, immobilized metal affinity chromatography (IMAC), size exclusion chromatography, polyacrylamide gel electrophoresis (PAGE), western blotting, surface plasmon resonance and mass spectroscopy.

Compositions comprising an inhibitor of the IL-33 pathway are also encompassed by the instant invention. In a particular embodiment, the composition further comprises a pharmaceutically acceptable carrier. The compositions may also comprise at least one other therapeutic as described hereinabove.

The IL-33 pathway inhibitor(s) (or composition(s) comprising the same) can be administered by any suitable route, for example, by injection (e.g., for local, direct, or systemic administration), oral, pulmonary, topical, nasal or other modes of administration. The composition may be administered by any suitable means, including parenteral, intramuscular, intravenous, intravascular, intraarterial, intraperitoneal, subcutaneous, topical, inhalatory, transdermal, intrapulmonary, intraareterial, intrarectal, intramuscular, and intranasal administration. In a particular embodiment, the composition is administered intraperitoneally. In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention (see, e.g., Remington's Pharmaceutical Sciences and Remington: The Science and Practice of Pharmacy). The pharmaceutical composition of the present invention can be prepared, for example, in liquid form, or can be in dried powder form (e.g., lyophilized for later reconstitution).

The therapeutic agents described herein will generally be administered to a patient as a pharmaceutical preparation. The term "patient" as used herein refers to human or animal subjects. The compositions of the instant invention may be employed therapeutically or prophylactically, under the guidance of a physician.

The compositions comprising the agent of the instant invention may be conveniently formulated for administration with any pharmaceutically acceptable carrier(s). The concentration of agent in the chosen medium may be varied and the medium may be chosen based on the desired route of administration of the pharmaceutical preparation. Except insofar as any conventional media or agent is incompatible with the agent to be administered, its use in the pharmaceutical preparation is contemplated.

The dose and dosage regimen of the agent according to the invention that is suitable for administration to a particular patient may be determined by a physician considering the patient's age, sex, weight, general medical condition, and the specific condition for which the agent is being administered to be treated or prevented and the severity thereof. The physician may also take into account the route of administration, the pharmaceutical carrier, and the agent's biological activity. Selection of a suitable pharmaceutical preparation will also depend upon the mode of administration chosen.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment or prevention therapy. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation or prevention of a particular condition may be determined by dosage concentration curve calculations, as known in the art.

The pharmaceutical preparation comprising the agent may be administered at appropriate intervals until the pathological symptoms are reduced or alleviated, after which the dosage may be reduced to a maintenance level. The appropriate interval in a particular case would normally depend on the condition of the patient. Toxicity and efficacy (e.g., therapeutic, preventative) of the particular formulas described herein can be determined by standard pharmaceutical procedures such as, without limitation, in vitro, in cell cultures, ex vivo, or on experimental animals. The data obtained from these studies can be used in formulating a range of dosage for use in human. The dosage may vary depending upon form and route of administration. Dosage amount and interval may be adjusted individually to levels of the active ingredient which are sufficient to deliver a therapeutically or prophylactically effective amount.

Definitions

The following definitions are provided to facilitate an understanding of the present invention:

The singular forms "a," "an," and "the" include plural referents unless the context clearly dictates otherwise.

As used herein, the terms "host," "subject," and "patient" refer to any animal, particularly mammals including humans.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions may be employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition (e.g., hemophagocytic lymphohistiocytosis or chimeric antigen receptor T-cell cytokine release syndrome) resulting in a decrease in the probability that the subject will develop the condition.

A "therapeutically effective amount" of a compound or a pharmaceutical composition refers to an amount effective to prevent, inhibit, or treat a particular disorder or disease and/or the symptoms thereof. For example, "therapeutically effective amount" may refer to an amount sufficient to modulate a cytokine related disease or disorder in a subject.

As used herein, the term "subject" refers to an animal, particularly a mammal, particularly a human.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule, and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

The following examples provide illustrative methods of practicing the instant invention, and are not intended to limit the scope of the invention in any way.

Example 1

Given the extensive tissue damage in HLH and the known role of CD8+ T-cells in the disease process, IL-33 signaling may be playing a heretofore unrecognized role in perpetuating disease and, therefore, be a novel target for therapy. The LCMV infected perforM deficient mouse model of HLH was used to test the role of IL-33. Notably, MyD88 and perforM double deficient mice were found to be protected from disease. Since IL-33 is known to signal through MyD88, this result supports a role for IL-33 in HLH.

In all experiments, mice were infected with $2 \times 10^5$ PFU of LCMV. Starting on day 3 following infection, mice were either treated with an IL-33 receptor neutralizing antibody (IL-33RB) (an antibody that was generated against the extracellular domain of ST2; see, e.g., Palmer et al. (2009) Arthritis Rheumat., 60:738-749) or isotype control antibody every other day (150 µg/dose i.p.).

Mice receiving IL-33RB treatment showed a survival advantage with a hazard ratio of 4 (p=0.06, log-rank test) (FIG. 1). Consistent with improved survival, mice treated with IL-33RB therapy showed a significant benefit in weight loss reduction (p=0.01, repeated measures 2-way ANOVA) in the initial phases of the disease (FIG. 2). Furthermore, IL-33RB treated mice showed a reduction in liver parenchyma damage (FIG. 3), but no reduction in inflammatory infiltrate. Il-33RB treated mice also showed a reduction/prevention of liver steatosis.

Given the known role of IFNγ in the pathogenesis of HLH, serum IFNγ levels were checked at day 11 post-infection of these mice. Serum IFNγ was highly significantly reduced over 16 fold in mice receiving IL-33RB treatment (p=0.0005, t-test) (FIG. 4). Thus, IL-33RB treatment shows an improvement in survival, weight loss, and hepatic injury, all concordant with a dramatic decrease in pathogenic serum IFNγ levels. Interestingly, despite improved survival, IL-33RB therapy did not affect the degree of the pan-cytopenia seen in these mice.

Immunosuppressive therapy is already in use for patients with HLH. However, such treatment protocols present treatment associated morbidity and mortality, particularly because the immune system is being suppressed in patients likely suffering from an active infection that triggered the HLH episode in the first place. In the case of wild type mice infected with LCMV, IL-33RB treatment results in a loss of antigen specific effector CD8+ T-cells (Bonilla et al. (2012) Science 335:984-9). This would not necessarily be desirable in patients trying to fight off an infection. Therefore, the effect of the IL-33RB blockade on the numbers of anti-LCMV CD8+ T-cells in the context of HLH was assessed using a tetramer specific for the LCMV immunodominant epitope gp33. Surprisingly, IL-33RB treatment did not cause a loss of gp33 specific CD8+ T-cells (FIG. 5A). However, IL-33RB did cause a reduction in the numbers of IFNγ producing CD8+ and CD4+ T-cells (FIG. 5B-C), consistent with the reduction of IFNγ in the serum. Significantly, these levels of IFNγ producing cells and the level of IFNγ in the serum are not reduced to zero, indicating that IL-33RB treatment may not eliminate all protection from infection, but rather reduce the IFNγ response of effector cells to a less toxic level to the organism. Thus, IL-33R blockade reduces serum IFNγ without abrogating the antigen-specific immune response.

As seen in FIG. 6, at 11 days post-infection, perforin KO mice treated with IL-33R blocking antibody have equivalent splenic titers of LCMV, compared to isotype-treated controls. This is consistent with the similar frequencies of LCMV-specific CD8+ T cells between the two treatment groups and shows that IL-33R blockade preserves the antiviral immune response while reducing excessive inflammation.

Example 2

Methods
Mice

Seven- to nine-week old male and female mice were used for these studies. C57BL/6 (WT) and perforin-deficient (C57BL/6-Prf1$^{tm1sth}$a, referred to as Prf1$^{-/-}$) mice were purchased from The Jackson Laboratory. MyD88$^{-/-}$ mice were obtained from The Children's Hospital of Philadelphia, Philadelphia, Pa. MyD88$^{-/-}$ mice were crossed to Prf1$^{-/-}$ mice (Adachi et al. (2000) Immunity 9(1):143-150). All mice were bred on a C57BL/6 background and housed in an animal facility certified by the Association for Assessment and Accreditation of Laboratory Animal Care.

Induction of FHL2

Mice were infected i.p. with 2×10$^5$ PFU LCMV-Armstrong on day 0. Mice were weighted and assessed daily for signs of morbidity. Mice were euthanized when moribund, when >20% starting body weight had been lost acutely (survival experiment), or when >30% starting body weight had been lost over several weeks (withdrawal experiment), according to our IACUC protocol. Peripheral blood was obtained by cheek bleed and complete blood cell counts were performed on a Hemavet® analyzer (Drew Scientific). Serum IFNγ levels were measured by ELISA (BD Biosciences). Viral titers 8 days post-infection (p.i.) were measured by plaque assay (Ahmed et al. (1984) J. Exp. Med., 160(2): 521-540).

Quantitative Real Time PCR

Organ sections from uninfected or LCMV-infected (7 days p.i.) WT and Prf1$^{-/-}$ mice were preserved in RNAlater® (Qiagen) and stored at −20° C. Tissues were homogenized in RLT lysis buffer (Qiagen) using a stator-rotor tissue homogenizer and RNA was isolated using RNeasy® Mini kit (Qiagen). cDNA was made using the SuperScript® III First-Strand Synthesis System (Life Technologies) according to the manufacturer's instructions. qRT-PCR was performed using QuantiTect® primers for Actb, Il33, and Il1rl1 (Qiagen) and Power SYBR® Green master mix (LifeTechnologies) on a StepOnePlus™ Real Time PCR System (Applied Biosystems). Results were normalized to β-actin using the ΔΔCT method.

Histology

Unperfused liver sections were fixed overnight in 4% paraformaldehyde and embedded in paraffin. Liver sections were stained with H&E and were read by a pediatric pathologist (PAK) blinded to treatment protocols. Microvesicular steatosis was assessed using a standardized scoring system as follows: 0—absent, 1—1-20% of area per 20× objective high power field, 2—21-40%, 3—41-60%, 4—61-80%, 5—81-100%. Lobular inflammation was scored as number of foci of lobular inflammation per 20× objective high power field in the most inflamed area. IL-33 immunohistochemistry was performed on slides after antigen retrieval with a pressure cooker. Mouse IL-33 Affinity Purified Polyclonal Ab was obtained from R&D Systems. Detection was performed using the Vectastain® ABC (rat) Kit (Vector Laboratories), followed by DAB reagent (Dako).

In Vivo ST2 Blockade

Rat IgG1 anti-mouse ST2-blocking antibody (referred to as α-ST2 antibody) and murine IgG1 isotype control peptibody (referred to as Control antibody) were obtained from Amgen (Palmer et al. (2009) Arthritis Rheumatism 60(3): 738-749). LCMV-infected mice were injected i.p. with 150 μg α-ST2 antibody or 150 μg control antibody on days 3, 5, and 7 p.i. Mice were euthanized on day 8 for analysis. For survival experiments, mice were injected with α-ST2 or control antibody beginning on day 3 and continuing every other day thereafter. For the withdrawal experiment, mice that had been treated with α-ST2 antibody until day 17 either continued to receive α-ST2 antibody every other day until day 29 or were switched to control antibody treatment at day 19.

Flow Cytometric Analysis

Spleens were harvested, homogenized, and passed through a 70-μm filter to generate single-cell suspensions. Red blood cells were lysed using ACK (ammonium-chloride-potassium) Lysing Buffer (Lonza). Cell concentrations were assessed using a hemocytometer or a Countess® Automated Cell Counter (Life Technologies). Cells were stained with LIVE/DEAD® fixable viability dye (Life Technologies) in PBS for 30 minutes at 4° C., washed twice, and stained with CD4, CD8α, CD44, CD45.1, CD62L, CD90.2, and/or CD127 fluorochrome-tagged antibodies (BD Pharmingen, eBioscience, BioLegend, and Miltenyi Biotec) in PBS 2% FBS for 30 minutes at 4° C. H-2D$^b$GP$_{33-41}$ and I-A$^b$GP$_{66-77}$ MHC-peptide complexes were provided as fluorophore-conjugated tetramers by the NIH Tetramer Core Facility. All samples were acquired on a MACSQuant® flow cytometer (Miltenyi Biotec) and analyzed using FlowJo software version 9.6 (Tree Star).

Intracellular Cytokine Staining

For intracellular cytokine analysis, 10$^6$ splenocytes were cultured in the absence or presence of LCMV GP33 peptide (0.2 μg/ml, GenScript) or LCMV GP61 peptide (1.0 μg/ml, Anaspec) and brefeldin A (Sigma) for 5 hours at 37° C. Following staining with LIVE/DEAD® and for surface antigens as described above, cells were stained for IFNγ (clone XMG1.2) using the Cytofix/Cytopenn™ kit (BD Bioscience) according to the manufacturer's instructions. To minimize carry-over of viral antigen in 2 of 3 experiment replicates, 0.3×10$^6$ T cells purified from LCMV-infected splenocytes by negative magnetic bead selection were plated with 0.7×10$^6$ uninfected C57BL/6.SJL splenocytes depleted of T cells by magnetic bead separation (Miltenyi Biotec). CD45.1$^+$ cells were excluded from subsequent flow analysis. Results were comparable with or without this additional T cell isolation step.

Statistical Analysis

Data were plotted and analyzed using Prism 5.0 (GraphPad Software). Symbols in figures represent individual mice, unless otherwise stated. Statistical significance was tested using two-way analysis of variance (ANOVA), Student's unpaired 2-tailed t-test, repeated-measures 2-way ANOVA, log-rank (Mantel-Cox) test, or linear mixed effects model, as appropriate. Weight loss data were analyzed by linear mixed effects models to allow for missing data due to mouse mortality. T cell data were also analyzed by linear mixed effects models to account for baseline variability between experimental replicates. For these analyses, R (R Core Team, 2014) and lme4 (Bates et al. (2014) lme4: Linear mixed-effects models using Eigen and S4, arXiv: 1406.5823v1) were used to perform a linear mixed effects analysis. For weight loss experiments, treatment and body weight were modeled as fixed effects, and individual mice were treated as a random effect to account for baseline variability between animals (e.g., intercept only). For T cell data, treatment and genotype were modeled as fixed effects, and experiment was treated as a random effect to account for baseline variability between experimental replicates (e.g., intercept only). Visual inspection of residual plots did not reveal any obvious deviations from homoscedasticity or normality. P-values were obtained by likelihood ratio tests of the full model with the effect in question against the model without the effect in question. The method of Levy (Levy R. Using R formulae to test for main effects in the presence of higher-order interactions. 2014; arXiv:stat.ME/ 1405.2094v1) was used to obtain tests of main effects while modeling an interaction effect. Unless otherwise specified, P values are represented in figures by number of symbols (e.g. *P<0.05, P<0.01, * P<0.001).

Study Approval

All animal studies were performed with the approval of The Children's Hospital of Philadelphia IACUC.

Results

Work in the related Jinx model of FHL type 3 has implicated a role for MyD88 signaling in FHL pathophysiology (Krebs et al. (2011) Blood 117(24):6582-6588). To confirm the importance of MyD88 signaling in the murine model of FHL2, the response of $Prf1^{-/-}$ and $Prf1^{-/-}MyD88^{-/-}$ mice to LCMV infection were compared. Similar to findings in Jinx mice, MyD88 deficiency protected $Prf1^{-/-}$ mice from death, anemia, thrombocytopenia, and hepatic inflammation. Consistent with these reduced FHL disease parameters, $Prf1^{-/-}MyD88^{-/-}$ mice had significantly decreased levels of serum IFNγ (FIG. 7A) and frequencies of $CD8^+$ T cells specific for the immunodominant LCMV epitope gp33. These results indicate that non-TCR signaling pathways such as MyD88 are important for promoting disease in the FHL2 murine model.

To further delineate the signaling mediators upstream of MyD88 that contribute to the development of FHL, signaling through receptors of the IL-1 family, which includes IL-1α, IL-1β, IL-18, and IL-33, were studied. While in vivo blockade of either IL-1 or IL-18 signaling has no effect on FHL mortality (Jordan et al. (2004) Blood 104(3):735-743; Jessen et al. (2013) Front. Immunol., 4:448), the role of IL-33 in FHL has not previously been investigated. IL-33 is constitutively expressed in the nuclei of epithelial cells, endothelial cells, fibroblasts, and other non-hematopoietic cells, and is released upon cellular stress or necrosis (Kakkar et al. (2012) J. Biol. Chem., 287(9):6941-6948; Moussion et al. (2008) PloS one 3(10):e3331; Pichery et al. (2012) J. Immunol., 188(7):3488-3495). Extracellular IL-33 subsequently signals by binding to its receptor (the ST2/IL1RAP complex), which is expressed by a diverse range of immune cells (Schmitz et al. (2005) Immunity 23(5):479-490; Chackerian et al. (2007) J. Immunol., 179(4):2551-2555; Mirchandani et al. (2012) Trends Immunol., 33(8):389-396). IL-33 is thus classified as an alarmin, in that it activates an inflammatory response in the context of tissue damage (Moussion et al. (2008) PloS one 3(10):e3331; Luthi et al. (2009) Immunity 31(1):84-98; Cayrol et al. (2009) PNAS 106(22):9021-9026). Furthermore, IL-33 promotes anti-viral $CD8+$ T cell differentiation and function (Yang et al. (2011) Eur. J. Immunol., 41(11):3351-3360; Bonilla et al. (2012) Science 335(6071):984-989). These facts led us to the conclusion that IL-33 signaling upstream of MyD88 contributes to FHL inflammation.

It was first determined whether IL-33 and its receptor are expressed in the organs most affected by FHL in LCMV-infected $Prf1^{-/-}$ mice (referred to as FHL2 mice). While hepatic expression of Il33 remained stable in both WT and $Prf1^{-/-}$ mice following LCMV infection, splenic Il33 was greatly upregulated in these mice after viral infection (FIG. 7B). Notably, Il33 expression was highest in the spleens of FHL2 mice; given the rough correlation demonstrated between splenic Il33 mRNA and LCMV titers in WT mice (Bonilla et al. (2012) Science 335(6071):984-989), this elevation may reflects the sustained viremia in FHL2 mice (Lykens et al. (2011) Blood 118(3):618-626; Matloubian et al. (1999) J. Virol., 73(3):2527-2536). Immunohistochemical analysis confirmed nuclear localization of IL-33 in cells of both the livers and spleens of WT and $Prf1^{-/-}$ mice (FIG. 7C). Although the spatial distribution and number of $IL-33^+$ cells did not change substantially after infection, IL-33-expressing cells in LCMV-infected tissue exhibited larger, rounder nuclei, consistent with a more activated status (FIG. 7C). Strikingly, expression of the specific component of the IL-33 receptor, ST2 (encoded by Il1rl1 was greatly increased in both the spleens and livers of FHL2 mice (FIG. 7D). Together, these results show that IL-33 and ST2 are highly expressed in FHL2 mice.

To probe the role of IL-33 in murine FHL, IL-33 signaling was disrupted in FHL2 mice by administration of an ST2-blocking antibody (α-ST2) and compared their survival to that of FHL2 mice receiving an isotype control antibody (Control). Remarkably, α-ST2-treated mice were significantly protected from mortality and severe weight loss compared to Control mice (FIGS. 8A, 8B). Continual ST2 blockade enabled mice to survive at least 30 days post-infection (p.i.) and limited weight loss even later in the course of disease (FIG. 8C). Additionally, α-ST2-treated mice showed less severe hematologic abnormalities, as anemia and thrombocytopenia were mitigated in these mice compared to Controls (FIG. 8D). Althoughα-ST2-treated and Control mice demonstrated similar levels of lobular inflammation in the liver, ST2 blockade significantly reduced hepatic parenchymal damage (FIG. 8E). The microvesicular steatosis evident in livers of Control but not α-ST2-treated mice indicates severe, acute metabolic impairment (Jaeschke et al. (2002) Toxicolog. Sci., 65(2): 166-176) and indicates worsened disease in Control mice. Despite multiple improved disease parameters in α-ST2-treated FHL2 mice, both treatment groups showed equivalently high LCMV titers in the spleen 8 days p.i. (FIG. 8F). Thus, disruption of IL-33 signaling reduces morbidity and mortality in murine FHL despite the persistence of virus at high titers. These results indicate that rather than modulating the infection, IL-33 instead modulates the pathologic immune response.

IL-33, in combination with IL-12, can induce IFNγ production by T cells and NK cells, and IL-33 is crucial for promoting CD8+ T cell effector functions such as cytokine production (Yang et al. (2011) Eur. J. Immunol., 41(11): 3351-3360; Bonilla et al. (2012) Science 335(6071):984-989; Bourgeois et al. (2009) Eur. J. Immunol., 39(4):1046-1055). Given the central role of IFNγ in FHL pathophysiology, ST2 blockade may reduce disease severity in FHL2 mice by diminishing systemic levels of IFNγ. α-ST2 treatment significantly decreased serum IFNγ in LCMV-infected WT mice, but its effect on FHL2 mice was far more striking, with a 16-fold reduction in IFNγ levels in these mice (FIG. 9A). These data demonstrate that ST2 blockade critically regulates a major pathogenic factor in FHL and indicate that IL-33 signaling is upstream of IFNγ production in FHL.

To determine how disruption of IL-33 signaling reduces systemic levels of IFNγ, the frequency and IFNγ production capacity of the lymphocyte populations was examined in this model. ST2 blockade decreased the number of $CD44^{hi}CD62L^{lo}CD127^{lo}$ effector $CD8^+$ T cells in FHL2 mice (2.4-fold reduction), although not to the degree seen in LCMV-infected WT mice (5.4-fold reduction) (FIG. 9B). Effector $CD4^+$ T cells were similarly reduced by α-ST2 treatment (1.7-fold reduction in FHL2 mice, 2.2-fold in LCMV-infected WT mice) (FIG. 9B). Numbers of $CD44^{hi}CD62L^{hi}CD127^{hi}$ memory-phenotype cells were only slightly altered by α-ST2 treatment in FHL2 mice (1.2-fold reduction in CD8+ T cells) or not at all (1.01-fold increase in CD4+ T cells). Numbers of NK cells were unaffected by ST2 blockade. Among effector-phenotype T cells, lower numbers of LCMV gp33-specific CD8+ T cells were found in α-ST2-treated FHL2 and LCMV-infected WT mice (FIG. 9C). Although the interaction between genotype and treatment did not reach statistical significance for numbers of gp33-specific $CD8^+$ T cells (p=0.054), there was a trend towards a greater α-ST2-mediated reduction of these cells in LCMV-infected WT mice (5.9-fold) than in FHL2 mice (2.1-fold) (FIG. 9C). Interestingly, LCMV gp61-specific $CD4^+$ T cells were reduced 3.5-fold by α-ST2 treatment in FHL2 mice only (FIG. 9C). Together, these findings indicate that IL-33 promotes the expansion and/or differentiation of LCMV-specific effector cells, which are known to be pathogenic in FHL2 mice. Furthermore, the magnitude of the suppressive effect mediated by ST2 blockade on effector $CD4^+$ and $CD8^+$ T cells is different between LCMV-infected WT and FHL2 mice, highlighting the aberrations in T cell regulation characteristic of FHL.

It was then investigated whether IL-33 signaling affects the ability of LCMV-specific effector cells to produce IFNγ by performing intracellular cytokine staining on T cells from LCMV-infected WT and FHL2 mice receiving either α-ST2 or Control antibody. Control FHL2 mice demonstrated higher frequencies of $IFNγ^+$ gp33-specific CD8+ T cells than Control LCMV-infected WT mice (FIG. 9D) (Jordan et al. (2004) Blood 104(3):735-743; Lykens et al. (2011) Blood 118(3):618-626). Remarkably, in vivo ST2 blockade significantly reduced the frequency of $IFNγ^+$gp33-specific $CD8^+$ T cells in both FHL2 and LCMV-infected WT mice to a similar degree (1.7- and 2.7-fold reductions, respectively) (FIG. 9D). Similar results were seen for $CD4^+$ T cells, with α-ST2 treatment inducing a 2.7-fold reduction in $IFNγ^+$ gp61-specific $CD4^+$ T cells in FHL2 mice and a 2.2-fold reduction in LCMV-infected WT mice (FIG. 9D). Furthermore, ST2 blockade reduced IFNγ responses by $CD8^+$ and $CD4^+$ T cells from FHL2 mice across a range of LCMV peptide concentrations. Additionally, significant reductions in IFNγ median fluorescence intensity (MFI) mediated by α-ST2 treatment in both IFNγ+LCMV-specific $CD8^+$ and $CD4^+$ T cells were found (FIG. 9E), indicating that in addition to reducing the frequency of IFNγ-producing cells, blockade of IL-33 signaling reduces the average per-cell production of this cytokine. Together, the decreased frequency of $IFNγ^+$ LCMV-specific $CD4^+$ and $CD8^+$ T cells and the reduced per-cell IFNγ production by these cells accounts for the low systemic IFNγ in α-ST2-treated FHL2 mice.

Thus, the data provided herein show a role for IL-33 signaling in FHL pathophysiology. These data demonstrate that adjuvant-like TCR-independent signals critically contribute to the hyperinflammation of FHL and indicate a revised model for this disease, in which excessive antigen is not the only stimulus driving immune dysregulation. The data point to an additional pathway of IL-33, likely released from damaged tissue, promoting T cell-mediated production of IFNγ, which continues to drive the feed-forward loop of immunopathologic inflammation in FHL.

This pathogenic IL-33/IFNγ axis provides an important point of manipulation for the treatment of FHL. While in vivo modulation of numerous pathways (including IL-1α, IL-1β, IL-10, IL-12, IL-18, TNFα, M-CSF, and GM-CSF signaling) has failed to demonstrate any therapeutic benefit in FHL mice, IFNγ and now IL-33 stand out as the only cytokines whose blockade significantly improves survival and disease severity. The data provide evidence for ST2 blockade as a viable therapeutic strategy in FHL. Disruption of IL-33 signaling reduces systemic IFNγ to sub-lethal levels without rendering FHL2 mice completely deficient in this key anti-viral cytokine (FIG. 9A); accordingly, viral control is not worsened in these mice (FIG. 8F). This approach may be safer than targeting IFNγ directly, as patients with disrupted IFNγ signaling show increased susceptibility to infection (Browne et al. (2010) Curr. Opin. Allergy Clin. Immunol., 10(6):534-541; Susan et al. (2000) Cytokine Growth Factor Rev., 11(4):321333). Furthermore, recently described cases of FHL occurring in patients with IFNγ receptor deficiency highlight the need for therapeutics designed to target a diverse range of pathways in FHL (Tesi et al. (2015) J. Allergy Clinical Immunol., 10.1016/j.jaci.2014.11.030).

Given the large degree of tissue damage observed in FHL2 mice (Jordan et al. (2004) Blood 104(3):735-743), it is likely that bioactive IL-33 is released by necrotic cells, consistent with its described role as an alarmin (Moussion et al. (2008) PloS one 3(10):e3331). However, LCMV is a non-cytopathic virus (Kagi et al. (1996) Curr. Opin. Immunol., 8(4):472-477), suggesting that direct viral effects are not responsible for the tissue necrosis observed in this model. Rather, it is likely that injury to cells results from the hyperactivated immune response, potentially via reactive oxygen species released by the activated macrophages that feature prominently in FHL2 mice (Jordan et al. (2004) Blood 104(3):735-743). Another possibility is that the coagulopathy present in FHL2 mice gives rise to thromboembolicischemia, leading to cellular necrosis. Recent reports have also highlighted the ability of non-lethal cellular stressors to induce secretion of IL-33 (Kakkar et al. (2012) J. Biol. Chem., 287(9):6941-6948; Kouzaki et al. (2011) J. Immunol., 186(7):4375-4387), an additional mechanism that may account for IL-33 release.

The findings reveal an ST2 signaling requirement of $CD8^+$ and $CD4^+$ T cells for IFNγ overproduction in FHL2 mice (FIGS. 9D, 9E). Although WT $CD8^+$ T cells upregulate ST2 after LCMV infection and their differentiation and function is regulated by IL-33 in a cell-intrinsic manner (Bonilla et al. (2012) Science 335(6071):984-989), the data presented here demonstrate differential effects of ST2 blockade in FHL2 mice. A wide range of immune cell subsets—including NK cells, macrophages, and dendritic cells—expresses ST2 (Garlanda et al. (2013) Immunity 39(6):1003-1018), suggesting the possibility of an intermediate IL-33-responsive cell in this pathway.

Based on the decisive role that IL-33 plays in promoting dysregulated immune responses in FHL2, IL-33 may also be an important driver of inflammation in other cytokine storm disorders. IL-33 may play a role in endotoxic shock (Oboki et al. (2010) PNAS 107(43):18581-18586) and hantavirus infection (Zhang et al. (2015) PLoS neglected tropical diseases 9(2):e0003514). Given the high degree of tissue damage evident in such hyperinflammatory diseases, systemic release of IL-33 may provide an additional amplifying signal that contributes to the feed-forward mechanism of immune dysregulation. Thus, α-ST2 therapy would benefit a broader range of immune-mediated diseases than the Th2-mediated disorders with which IL-33 is classically identified. In summary, it has been shown that disruption of IL-33 signaling in the murine model of FHL reduces T cell-mediated production of IFNγ, leading to improved morbidity and mortality, and indicates blockade of this pathway as a viable treatment strategy for FHL.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for inhibiting or treating a cytokine-related disease or disorder in a subject, said method comprising administering to a subject an IL-33 pathway inhibitor,
   wherein said cytokine-related disease or disorder is hemophagocytic lymphohistiocytosis, and
   wherein said IL-33 pathway inhibitor is an antibody or fragment thereof immunologically specific for IL-33 receptor (IL-33R).

2. The method of claim 1, wherein said method further comprises administering a hemophagocytic lymphohistiocytosis therapy selected from the group consisting of an immunosuppressant, glucocorticoid, cyclosporine A, etoposide, methotrexate, IL-1 blocking agent, rilonacept, canakinumab, and gevokizumab.

3. The method of claim 1, wherein said method further comprises performing a bone marrow transplant on said subject.

4. The method of claim 1, wherein said hemophagocytic lymphohistiocytosis is familial (primary) hemophagocytic lymphohistiocytosis (FHL).

5. The method of claim 1, wherein said hemophagocytic lymphohistiocytosis is secondary hemophagocytic lymphohistiocytosis (SHLH).

6. The method of claim 1, wherein said hemophagocytic lymphohistiocytosis is malignancy associated hemophagocytic lymphohistiocytosis.

7. The method of claim 1, wherein said antibody or fragment thereof is immunologically specific for the extracellular domain of IL-33R.

8. The method of claim 1, wherein said method comprises administering an antibody immunologically specific for IL-33R to the subject.

9. The method of claim 1, wherein said method comprises administering an antibody immunologically specific for the extracellular domain of IL-33R to the subject.

* * * * *

UNITED STATES PATENT AND TRADEMARK OFFICE
CERTIFICATE OF CORRECTION

Page 1 of 1

PATENT NO.       : 10,040,859 B2
APPLICATION NO.  : 15/305272
DATED            : August 7, 2018
INVENTOR(S)      : Edward M. Behrens, Julia E. Rood and Taku Kambayashi It is certified that error appears in the above-identified patent and that said Letters Patent is hereby corrected as shown below:

In the Specification

At Column 1, Lines 15-17:
Please delete:
"Grant No. HL112836-01A1 awarded by the National Heart, Lung, and Blood Institute. The Government has certain rights in this invention."

And insert therefor:
--grant number HL112836 awarded by the National Institutes of Health. The government has certain rights in the invention.--

Signed and Sealed this
Tenth Day of March, 2020

Andrei Iancu
*Director of the United States Patent and Trademark Office*